United States Patent
Boyd

(10) Patent No.: US 10,327,944 B2
(45) Date of Patent: Jun. 25, 2019

(54) DENTAL MOUTHPIECE FOR TREATING SNORING OR APNEA AND METHOD OF ASSEMBLY

(71) Applicant: James Palmer Boyd, Rancho Santa Fe, CA (US)

(72) Inventor: James Palmer Boyd, Rancho Santa Fe, CA (US)

( * ) Notice: Subject to any disclaimer, the term of this patent is extended or adjusted under 35 U.S.C. 154(b) by 554 days.

(21) Appl. No.: 14/885,871

(22) Filed: Oct. 16, 2015

(65) Prior Publication Data
US 2016/0120690 A1    May 5, 2016

Related U.S. Application Data

(60) Provisional application No. 62/075,513, filed on Nov. 5, 2014.

(51) Int. Cl.
*A61F 5/56* (2006.01)

(52) U.S. Cl.
CPC .................................... *A61F 5/566* (2013.01)

(58) Field of Classification Search
CPC .... A61C 7/08; A61C 7/36; A61C 7/14; A61F 5/56; A61F 5/566; A61F 2005/563
USPC ................ 128/848, 861, 862; 433/140, 6, 8; 602/902
See application file for complete search history.

(56) References Cited

U.S. PATENT DOCUMENTS

| | | | | |
|---|---|---|---|---|
| 4,059,101 A | * | 11/1977 | Richmond | A61H 13/00 601/139 |
| 6,845,774 B2 | * | 1/2005 | Gaskell | A61F 5/566 128/848 |
| 2011/0195376 A1 | | 8/2011 | Boyd, Sr. | |
| 2012/0216820 A1 | * | 8/2012 | Scarberry | A61F 5/566 128/848 |
| 2012/0255559 A1 | * | 10/2012 | Thornton | A61F 5/566 128/848 |

* cited by examiner

*Primary Examiner* — Ophelia A Hawthorne
*Assistant Examiner* — Caitlin A Carreiro
(74) *Attorney, Agent, or Firm* — Plager Schack LLP; Mark H. Plager; Eric Liou

(57) ABSTRACT

A dental mouthpiece for use in treating snoring or apnea of a user is used with a hook mechanism that engages with a bracket when placed in the mouth. The mouthpiece includes a tray assembly having an upper tray and a lower tray, each of the upper and lower trays having a generally U-shape member extending along any one of the user's pair of dental arches and having a cutout, the upper tray's cutout able to receive the hook mechanism and the lower tray's cutout able to receive the bracket, and an adaptable resin disposed on top surfaces of the upper and lower trays. The tray assembly is oriented to permit the adaptable resin of the upper and lower trays to contact the user's dental arches. The hook mechanism engages with the bracket to enable the dental mouthpiece to maintain an open airway in the user's mouth.

12 Claims, 4 Drawing Sheets

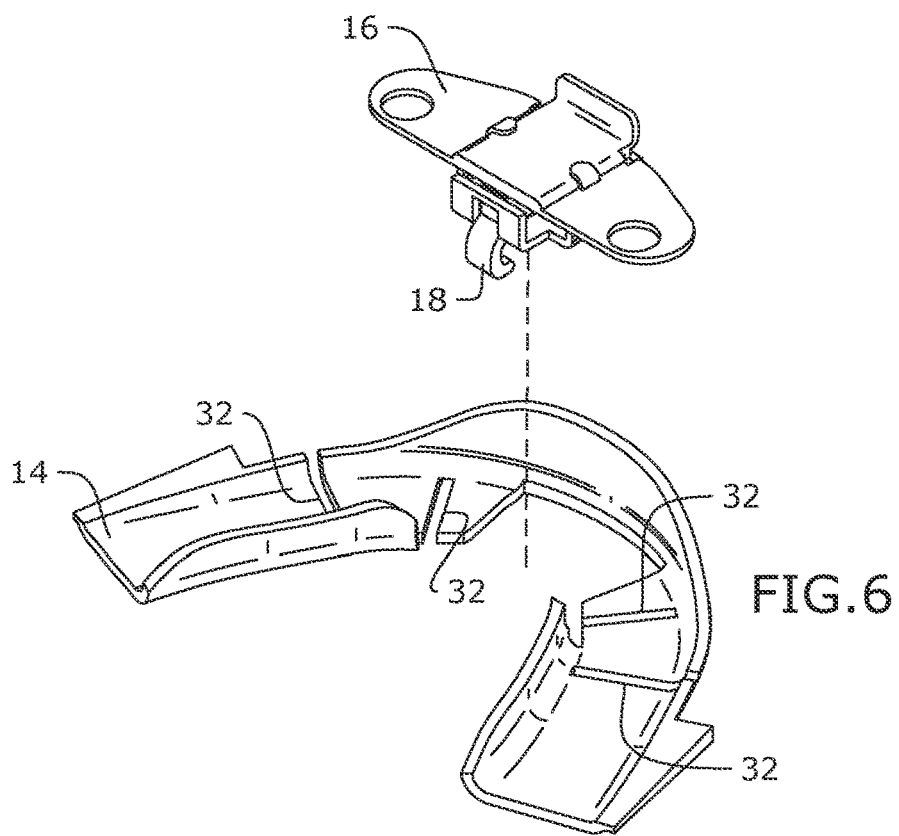
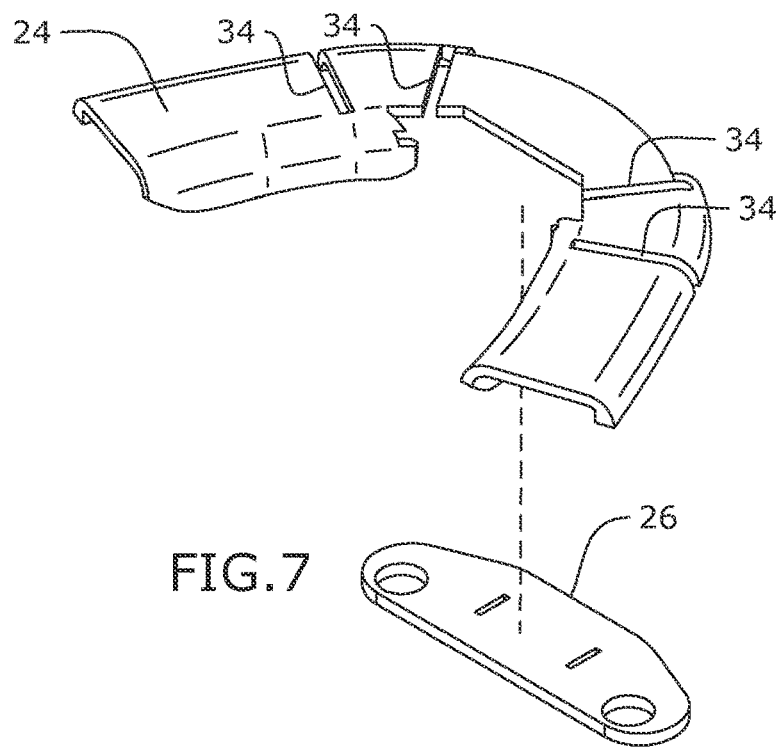

DENTAL MOUTHPIECE FOR TREATING SNORING OR APNEA AND METHOD OF ASSEMBLY

RELATED APPLICATION

The application claims priority to provisional patent application U.S. Ser. No. 62/075,513 filed on Nov. 5, 2014, the entire contents of which is herein incorporated by reference.

BACKGROUND

The embodiments herein relate generally to mouthpieces designed to treat apnea and/or snoring.

Current protocol for a dentist to deliver an FDA cleared mouthpiece for obstructive sleep apnea and/or snoring dictates that the dentist must take molds of the patient's teeth. These plaster teeth models are shipped to a professional dental laboratory. The laboratory process then incorporates an FDA cleared mechanism into customized mouthpieces based on the teeth models. Currently, these customized mouthpieces are constructed in a laboratory setting, then shipped back to the dentist. Lab fees can range anywhere from $150 to $400 to the dentist, depending on the nature and propriety of the mechanism used.

The dentist must then re-schedule a delivery appointment with the patient. Because the mouthpieces were made indirectly on models that were made from molds that may not be perfect representations of the patient's dental arches, the dentist must be prepared to adjust, modify and retrofit the mouthpieces to fit the patient comfortably. This is particularly common because an individual's teeth may shift naturally in response to forces generated by nighttime teeth grinding.

Following delivery of the mouthpieces, the patient must be able to tolerate and comply with the mouthpiece's prescribed use. A percentage of patients simply cannot tolerate having their lower jaw held in an open and forward fashion, and soon discontinue use.

Both the dentist and patients assume considerable financial risks. There is no way for the dentist to know if the patient will be able to tolerate the unnatural and strained position resulting from use of the mouthpieces to hold the lower jaw in, nor can he/she determine if the mouthpieces will in fact be therapeutic.

As such, there is a need in the industry for a custom dental mouthpiece for use in treating obstructive sleep apnea and/or snoring that addresses the limitations of the prior art. In particular, there is a need for an effective customized dental mouthpiece that can be assembled in the office with enhanced efficiency and reduced costs, without requiring additional laboratory time and expenses.

SUMMARY

A dental mouthpiece with enhanced durability for use in treating snoring or apnea of a user is provided. The dental mouthpiece is configured for use with a hook mechanism that engages with a bracket when placed in a mouth of the user. The dental mouthpiece comprises a tray assembly comprising an upper tray and a lower tray, each of the upper and lower trays comprising a generally U-shape member configured to extend along any one of a pair of dental arches of the user and comprising a cutout proximate a central portion of the member, the cutout of the upper tray being configured to receive the hook mechanism and the cutout of the lower tray being configured to receive the bracket, and an adaptable resin disposed on top surfaces of the upper and lower trays, wherein the tray assembly is disposed within the user's mouth and oriented to permit the adaptable resin of the upper and lower trays to contact the dental arches of the user, wherein the hook mechanism engages with the bracket, thereby enabling the dental mouthpiece to maintain an open airway in the user's mouth.

In certain embodiments, a method for assembling a dental mouthpiece for treating snoring or apnea of a user with enhanced efficiency and reduced cost is provided. The method comprises providing a tray assembly described above, inserting the hook mechanism in the cutout of the upper tray, inserting the bracket in the cutout of the lower tray, applying a heated resin to top surfaces of the upper and lower trays, disposing the heated resin of the upper tray on an upper dental arch of the user to permit the heated resin to adapt to contours of upper teeth of the user, and disposing the heated resin of the lower tray on a lower dental arch of the user to permit the heated resin to adapt to contours of lower teeth of the user.

BRIEF DESCRIPTION OF THE FIGURES

The detailed description of some embodiments of the invention will be made below with reference to the accompanying figures, wherein the figures disclose one or more embodiments of the present invention.

FIG. 6 depicts an exploded view of certain embodiments of the dental mouthpiece;

FIG. 7 depicts an exploded view of certain embodiments of the dental mouthpiece.

DETAILED DESCRIPTION OF CERTAIN EMBODIMENTS

Figure 1:
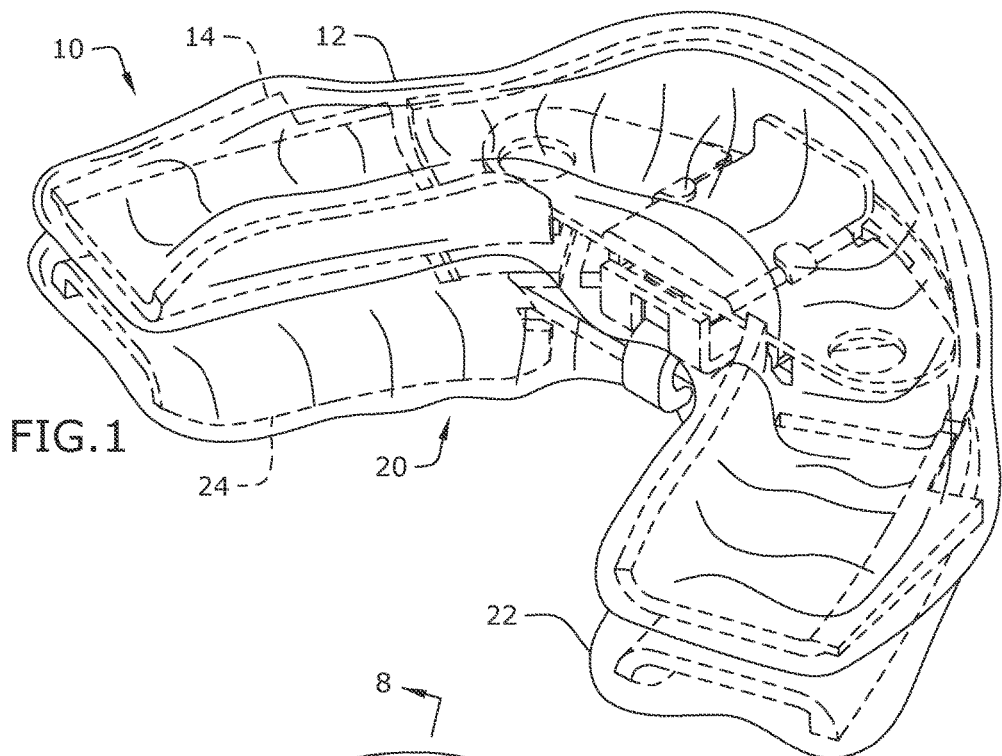
FIG. 1 depicts a rear upper perspective view of certain embodiments of the dental mouthpiece.
Figure 2:
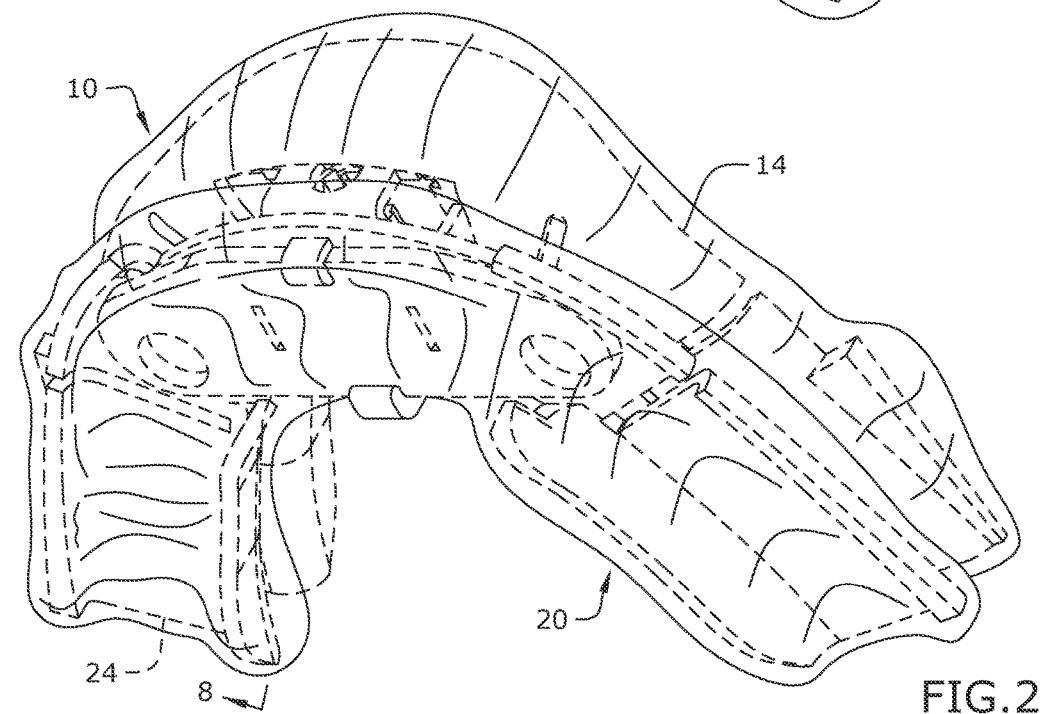
FIG. 2 depicts a front lower perspective view of certain embodiments of the dental mouthpiece.
Figure 3:
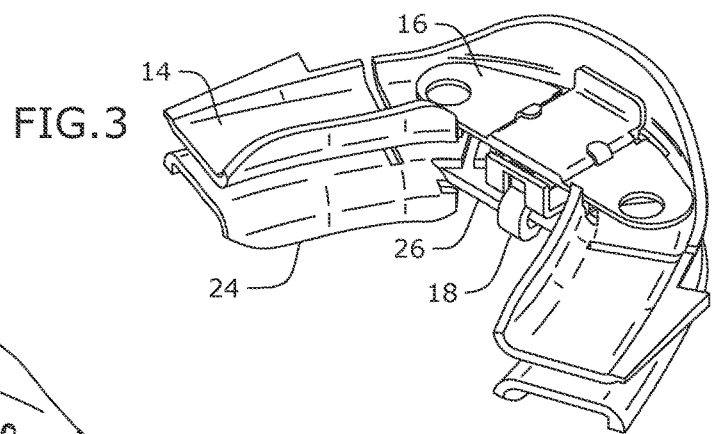
FIG. 3 depicts a rear upper perspective view of certain embodiments of the dental mouthpiece without the resin for illustrative clarity.
Figure 4:
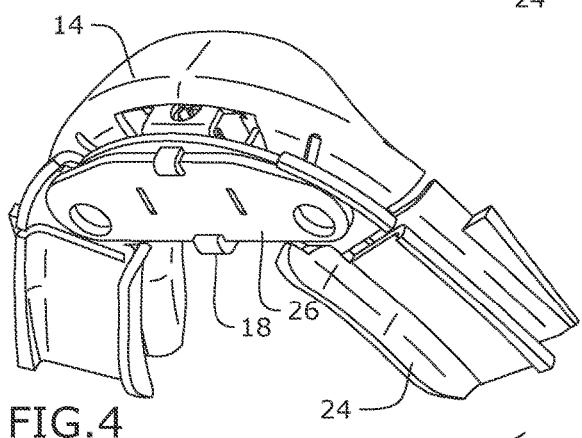
FIG. 4 depicts a front lower perspective view of certain embodiments of the dental mouthpiece without the resin for illustrative clarity.
Figure 5:
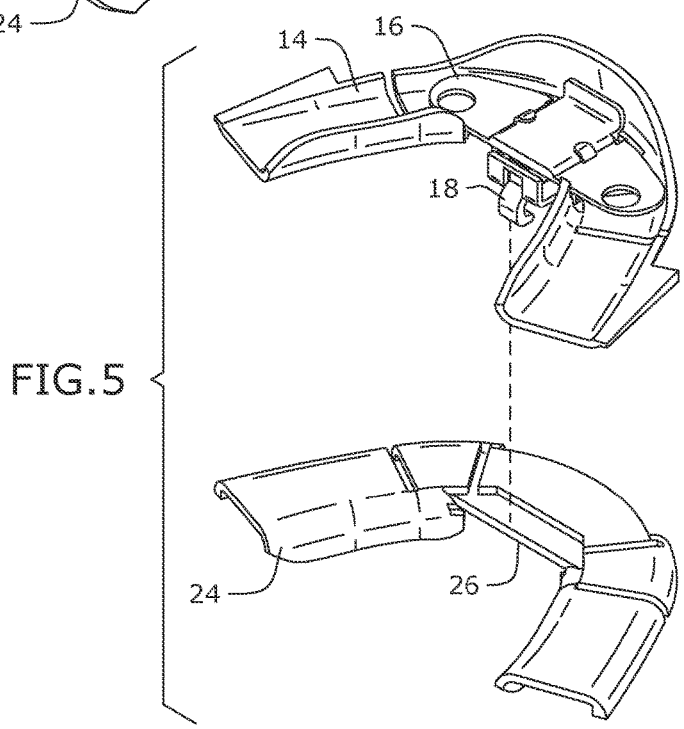
FIG. 5 depicts an exploded view of certain embodiments of the dental mouthpiece without the resin for illustrative clarity.

As depicted in FIGS. 1-2, the dental mouthpiece is configured to treat obstructive sleep apnea and/or snoring by maintaining an open airway within the user's mouth. The dental mouthpiece comprises upper tray assembly 10 and lower tray assembly 20, which are configured to be placed together and disposed within the user's mouth (not shown in these figures). Upper tray assembly 10 comprises upper tray 14 and upper tray resin 12. Similarly, lower tray assembly 20 comprises lower tray 24 and lower tray resin 22.

As depicted in FIGS. 3-7, upper tray 14 and lower tray 24 each comprises a generally U-shaped member that is configured to extend along any one of the user's dental arches. Upper tray 14 comprises upper tray indentations 32 configured to permit the tray to bend in order to accommodate the user's upper dental arch. Likewise, lower tray 24 comprises lower tray indentations 34 configured to permit the tray to bend in order to accommodate the user's lower dental arch. Although the figures depict four indentations for each tray, it shall be appreciated that any alternative number and/or orientation of indentations may be used to vary the flexibility of the tray. In a preferred embodiment, each tray is made from polycarbonate plastic and has a width of no greater than approximately three millimeters.

As depicted in FIGS. 6-7, upper tray 14 and lower tray 24 each comprises a cutout positioned at a central portion located at the anterior midline of the tray. This cutout is designed to receive any type of fastening mechanisms known in the field. In particular, upper tray 14 is configured to receive upper tray bracket 16, which comprises upper tray bracket hook 18. Lower tray 24 is configured to receive lower tray bracket 26. It shall be appreciated that upper tray 14 and lower tray 24 may each have a set of slots proximate the cutout configured to secure upper tray bracket 16 or lower tray bracket 26 in place.

In an assembled configuration as depicted in FIGS. 1-2, upper tray resin 12 is disposed on a top surface of upper tray 14. Lower tray resin 22 is disposed on a top surface of lower tray 24. In a preferred embodiment, upper tray resin 12 and lower tray resin 22 are both made from a thermoplastic resin. However, any alternative type of adaptable resin or putty may be used such as other chemical cure resins.

The dental mouthpiece may be assembled and used by implementing various steps. In certain embodiments of the invention, upper tray 14 and lower tray 24 are created from polycarbonate plastic through an injection mold process. Alternatively, upper tray 14 and lower tray 24 may be cut from a sheet to create the desired shape.

Upper tray 14 is bent as permitted by upper tray indentations 32 to modify its arch width to accommodate the width of the user's upper dental arch. Upper tray bracket 16 is secured to the cutout of upper tray 14. In this secured position, upper tray bracket hook 18 is positioned within the interior space defined by the U-shape member of upper tray 14. Upper tray resin 12 is heated to a putty stage and disposed on the top of upper tray 14 and upper tray bracket 16. Upper tray assembly 10 is disposed on the user's upper dental arch or a model of the user's upper dental arch. By placing upper tray resin 12 against the dental arch, the heated resin adapts to contours of teeth in the upper jaw. Upper tray resin 12 should be heated to a temperature that is sufficient to permit the resin to flow around the dentition, but not a temperature that is uncomfortable and/or harmful to the user.

Lower tray 24 is assembled in substantially the same manner as described for upper tray 14. Lower tray 24 is bent as permitted by lower tray indentations 34 to modify its arch width to accommodate the width of the user's lower dental arch. Lower tray bracket 26 is secured to the cutout of lower tray 24. Lower tray resin 22 is heated to a putty stage and disposed on the top of lower tray 24 and lower tray bracket 26. Lower tray assembly 20 is disposed on the user's lower dental arch or a model of the user's lower dental arch. By placing lower tray resin 22 against the dental arch, the heated resin adapts to contours of teeth in the lower jaw.

Figure 8:
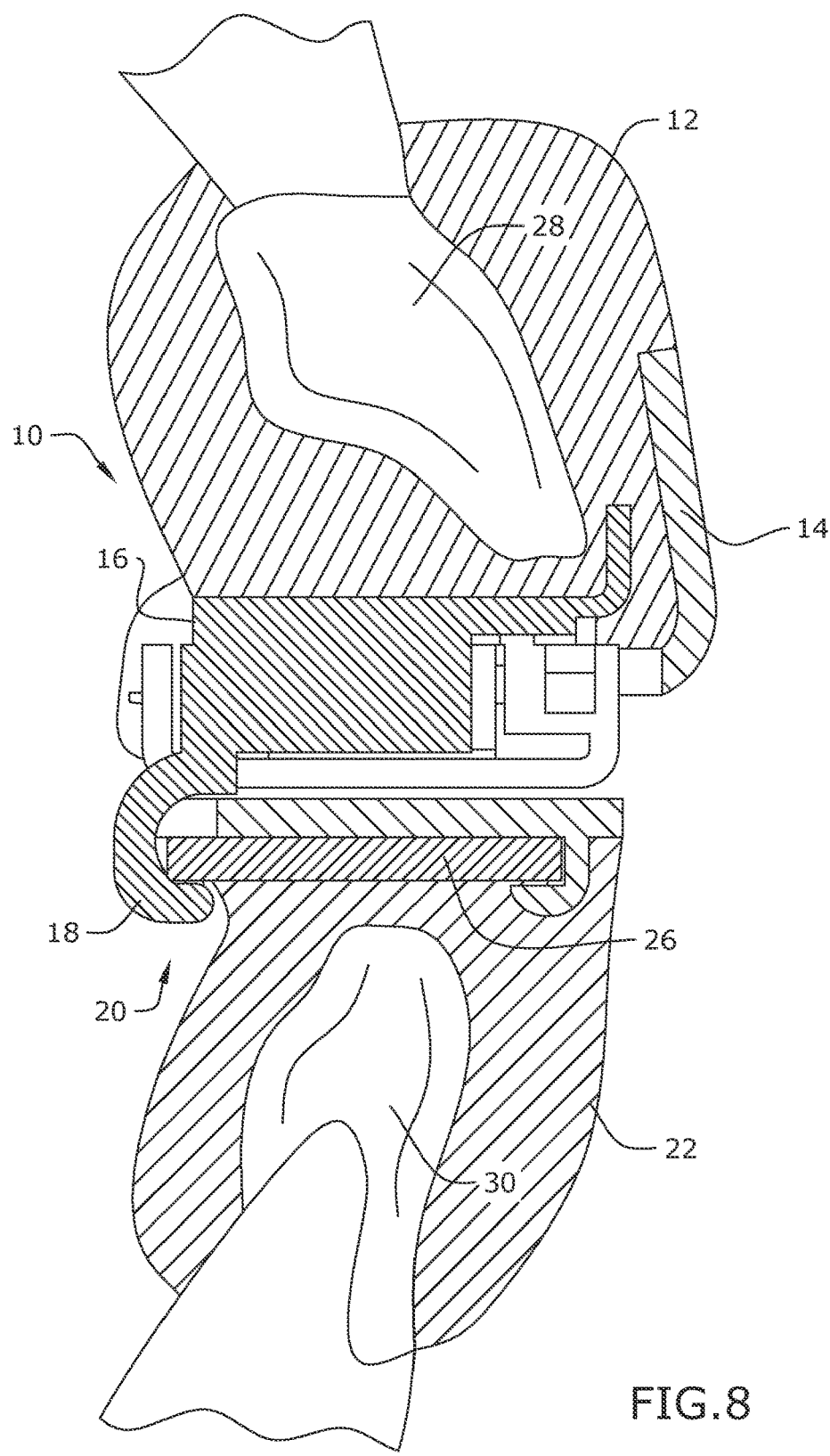
FIG. 8 depicts a section view of certain embodiments of the dental mouthpiece taken along line 8-8 in FIG. 2 in an exemplary usage.

Upper tray assembly 10 and lower tray assembly 20 are both removed from the patient's dental arches or model of dental arches just prior to the final cooling (curing) of upper tray resin 12 and lower tray resin 22. Once upper tray resin 12 and lower tray resin 22 are cooled to room temperature, upper tray assembly 10 and lower tray assembly 20 are inserted into the user's mouth as depicted in FIG. 8. In this position, upper tray resin 12 contacts the user's upper teeth such as exemplary upper tooth 28. Lower tray resin 22 contacts the user's lower teeth such as exemplary lower tooth 30. Upper tray bracket hook 18 engages the bottom of lower tray bracket 26. In this configuration, lateral movement of upper tray assembly 10 and lower tray assembly 20 is permitted within the user's mouth. However, upper tray bracket hook 18 prevents backward movement of lower tray assembly 20 in the user's mouth. In use, the dental mouthpiece maintains an open airway within the user's mouth, which helps to treat obstructive sleep apnea and/or snoring.

It shall be appreciated that the dental mouthpiece provides an effective customized dental mouthpiece solution that can be assembled in the office efficiently and with reduced costs. It shall be appreciated that the components of the dental mouthpiece described in several embodiments herein may comprise any alternative known materials in the field and be of any color, size and/or dimensions. It shall be appreciated that the components of the dental mouthpiece described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A dental mouthpiece with enhanced durability for use in treating snoring or apnea of a user, the dental mouthpiece configured for use with a hook mechanism that engages with a bracket when placed along a pair of dental arches in a mouth of the user, the dental mouthpiece comprising:

a tray assembly comprising an upper tray and a lower tray, each of the upper and lower trays comprising a generally U-shape member with a top surface, a bottom surface opposite the top surface, an inner side edge and an outer side edge opposite the inner side edge, the U-shape member of each tray in the upper and lower trays configured to extend along any one of the pair of dental arches of the user and comprising a cutout proximate a central portion of the member, the cutout of each tray in the upper and lower trays extending entirely through the U-shape member from the top surface to the bottom surface of the tray to create unobstructed space within the tray, thereby permitting the cutout of the upper tray to receive the hook mechanism therein and the cutout of the lower tray to receive the bracket therein;

a plurality of slits disposed on each tray in the upper and lower trays, the plurality of slits in each tray in the upper and lower trays comprising a first pair of slits on opposing sides of the cutout extending horizontally from the inner side edge of each tray to a first intermediate portion of the tray and a second pair of slits on opposing sides of the cutout extending horizontally from the outer side edge of each tray to a second intermediate portion of the tray, each slit in the first pair of slits positioned a first distance away from the cutout in the tray and each slit in the second pair of slits positioned a second distance away from the cutout in the tray, wherein the first distance is less than the second distance; and an adaptable resin disposed on top surfaces of the upper and lower trays, wherein the tray assembly is configured to be disposed within the user's mouth and oriented so that the adaptable resin of the upper and lower trays is configured to contact the dental arches of the user, wherein the hook mechanism engages with the bracket, thereby enabling the dental mouthpiece to maintain an open airway in the user's mouth.

2. The dental mouthpiece of claim 1, wherein the upper and lower trays are made from polycarbonate plastic.

3. The dental mouthpiece of claim 2, wherein the upper tray comprises a first set of slots proximate the cutout for receiving the hook mechanism and the lower tray comprises a second set of slots proximate the cutout for receiving the bracket.

4. The dental mouthpiece of claim 3, wherein the adaptable resin is a thermoplastic resin.

5. A method for assembling a dental mouthpiece for treating snoring or apnea of a user with enhanced efficiency and reduced cost, the dental mouthpiece configured for use with a hook mechanism that engages with a bracket when placed in a mouth of the user, the method comprising:
   providing a tray assembly, the tray assembly comprising:
      an upper tray and a lower tray, each of the upper and lower trays comprising a generally U-shape member with a top surface, a bottom surface opposite the top surface, an inner side edge and an outer side edge opposite the inner side edge, the U-shape member of each tray in the upper and lower trays configured to extend along any one of the pair of dental arches of the user and comprising a cutout proximate a central portion of the member, the cutout of each tray in the upper and lower trays extending entirely through the U-shape member from the top surface to the bottom surface of the tray to create unobstructed space within the tray; and
      a plurality of slits disposed on each tray in the upper and lower trays, the plurality of slits in each tray in the upper and lower trays comprising a first pair of slits on opposing sides of the cutout extending horizontally from the inner side edge of each tray to a first intermediate portion of the tray and a second pair of slits on opposing sides of the cutout extending horizontally from the outer side edge of each tray to a second intermediate portion of the tray, each slit in the first pair of slits positioned a first distance away from the cutout in the tray and each slit in the second pair of slits positioned a second distance away from the cutout in the tray, wherein the first distance is less than the second distance;
   inserting the hook mechanism in the cutout of the upper tray;
   inserting the bracket in the cutout of the lower tray;
   applying a heated resin to top surfaces of the upper and lower trays;
   disposing the heated resin of the upper tray on an upper dental arch of the user to permit the heated resin to adapt to contours of upper teeth of the user; and
   disposing the heated resin of the lower tray on a lower dental arch of the user to permit the heated resin to adapt to contours of lower teeth of the user.

6. The method of claim 5, further comprising flexing the upper tray to accommodate a first width of the upper dental arch of the user, and flexing the lower tray to accommodate a second width of the lower dental arch of the user.

7. The method of claim 6, further comprising removing the upper and lower trays from the dental arches of the user prior to a curing of the heated resin on the upper and lower trays.

8. The method of claim 7, further comprising disposing the tray assembly within the user's mouth, orienting the tray assembly to permit the resin of the upper tray to contact the upper dental arch and the resin of the lower tray to contact the lower dental arch, and engaging the hook mechanism with the bracket.

9. A dental mouthpiece with enhanced durability for use in treating snoring or apnea of a user, the dental mouthpiece configured for use with a hook mechanism that engages with a bracket when placed along a pair of dental arches in a mouth of the user, the dental mouthpiece comprising:
   a tray assembly comprising an upper tray and a lower tray, each of the upper and lower trays comprising a generally U-shape member with a top surface, a bottom surface opposite the top surface, an inner side edge and an outer side edge opposite the inner side edge, the U-shape member of each tray in the upper and lower trays configured to extend along any one of the pair of dental arches of the user and comprising a cutout proximate a central portion of the member, the cutout of each tray in the upper and lower trays extending entirely through the U-shape member from the top surface to the bottom surface of the tray to create unobstructed space within the tray to permit the cutout of the upper tray to receive the hook mechanism therein and the cutout of the lower tray to receive the bracket therein, each tray of the upper and lower trays comprising a plurality of slits disposed in the generally U-shape member to permit each tray to flex, the plurality of slits of each tray in the upper and lower trays comprising a first pair of slits on opposing sides of the cutout extending horizontally from the inner side edge of each tray to a first intermediate portion of the tray and a second pair of slits on opposing sides of the cutout extending horizontally from the outer side edge of each tray to a second intermediate portion of the tray, wherein each slit in the first pair of slits in each tray is positioned between the cutout of the tray and one of the pair of slits in the second pair of slits in each tray, each slit in the first pair of slits positioned a first distance away from the cutout in the tray and each slit in the second pair of slits positioned a second distance away from the cutout in the tray, wherein the first distance is less than the second distance; and
   an adaptable resin disposed on top surfaces of the upper and lower trays, wherein the tray assembly is configured to be disposed within the user's mouth and oriented so that the adaptable resin of the upper and lower trays is configured to contact the dental arches of the user, wherein the hook mechanism engages with the bracket, thereby enabling the dental mouthpiece to maintain an open airway in the user's mouth.

10. The dental mouthpiece of claim 9, wherein each slit in the first and second pairs of slits in each tray in the upper and lower trays comprises a first-sized unobstructed space within the tray and each cutout in each tray in the upper and lower trays comprises a second-sized unobstructed space within the tray, wherein the second-sized unobstructed space is greater than the first-sized unobstructed space.

11. A dental mouthpiece with enhanced durability for use in treating snoring or apnea of a user, the dental mouthpiece configured for use with a hook mechanism that engages with a bracket when placed along a pair of dental arches in a mouth of the user, the dental mouthpiece comprising:
   a tray assembly comprising an upper tray and a lower tray, each of the upper and lower trays comprising a continuous generally U-shape member with a top surface, a bottom surface opposite the top surface, an inner side edge and an outer side edge opposite the inner side edge, the U-shape member of each tray in the upper and lower trays configured to extend along any one of the pair of dental arches of the user and comprising a cutout proximate a central portion of the member, the cutout of each tray in the upper and lower trays extending entirely through the U-shape member from the top surface to the bottom surface of the tray to create unobstructed space within the tray, thereby permitting the cutout of the upper tray to receive the hook mechanism therein and the cutout of the lower tray to receive the bracket therein, the upper tray comprising an outer flange coupled to the outer side edge of the U-shape member and extending along a periphery of the cutout in the upper tray and a pair of inner flanges coupled to the inner side edge of the U-shape member on opposing sides of the cutout in the upper tray;

a plurality of slits disposed on each tray in the upper and lower trays, the plurality of slits in each tray in the upper and lower trays comprising a first pair of slits on opposing sides of the cutout extending horizontally from the inner side edge of each tray to a first intermediate portion of the tray and a second pair of slits on opposing sides of the cutout extending horizontally from the outer side edge of each tray to a second intermediate portion of the tray, each slit in the first pair of slits positioned a first distance away from the cutout in the tray and each slit in the second pair of slits positioned a second distance away from the cutout in the tray, wherein the first distance is less than the second distance; and an adaptable resin disposed on top surfaces of the upper and lower trays, wherein the tray assembly is configured to be disposed within the user's mouth and oriented so that the adaptable resin of the upper and lower trays is configured to contact the dental arches of the user, wherein the hook mechanism engages with the bracket, thereby enabling the dental mouthpiece to maintain an open airway in the user's mouth.

12. The dental mouthpiece of claim 11, wherein each inner flange in the pair of inner flanges extends along the inner side edge of the upper tray from a top edge of the U-shaped member to a location in between one of the first pair of slits and one of the second pair of slits.

* * * * *